(12) United States Patent  (10) Patent No.: US 9,259,213 B1
O'Hara  (45) Date of Patent: Feb. 16, 2016

(54) RETRACTOR

(71) Applicant: Thomas E. O'Hara, Troy, MI (US)

(72) Inventor: Thomas E. O'Hara, Troy, MI (US)

(73) Assignee: Thomas E. O'Hara, Troy, MI (US)

( * ) Notice: Subject to any disclaimer, the term of this patent is extended or adjusted under 35 U.S.C. 154(b) by 157 days.

(21) Appl. No.: 13/949,760

(22) Filed: Jul. 24, 2013

Related U.S. Application Data

(60) Provisional application No. 61/675,007, filed on Jul. 24, 2012.

(51) Int. Cl.
*A61B 17/12* (2006.01)
*A61B 17/02* (2006.01)
*A61B 17/70* (2006.01)
*A61B 17/88* (2006.01)

(52) U.S. Cl.
CPC .............. *A61B 17/02* (2013.01); *A61B 17/025* (2013.01); *A61B 17/7077* (2013.01); *A61B 17/88* (2013.01)

(58) Field of Classification Search
CPC .. A61B 17/025; A61B 17/7077; A61B 17/88; A61B 17/0218; A61B 17/02
See application file for complete search history.

(56) References Cited

U.S. PATENT DOCUMENTS 6,099,547 A * 8/2000 Gellman et al. .............. 606/198

* cited by examiner

*Primary Examiner* — Christian Sevilla
(74) *Attorney, Agent, or Firm* — Emch, Schaffer, Schaub & Porcello, Co., L.P.A.

(57) ABSTRACT

The proposed retractor blade is designed to function with a number of the currently available retractor systems with only minor modifications to those systems. The retractor blade has a hinge allowing it to flex and thereby allow a lateral approach to the discs at L1-L2 and L4-L5 despite the angle to these discs caused by coming in under the ribs or over the iliac crest.

17 Claims, 6 Drawing Sheets

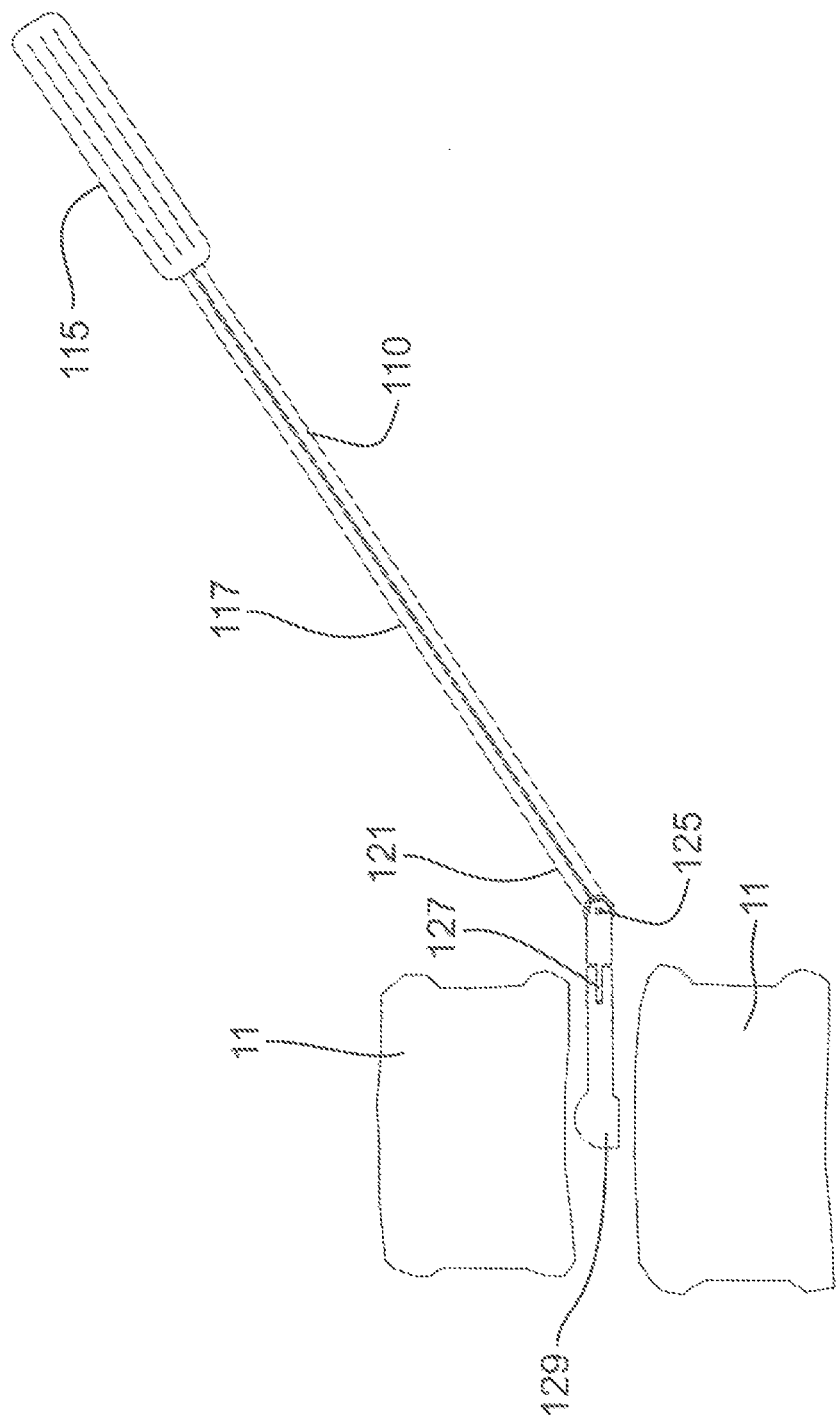

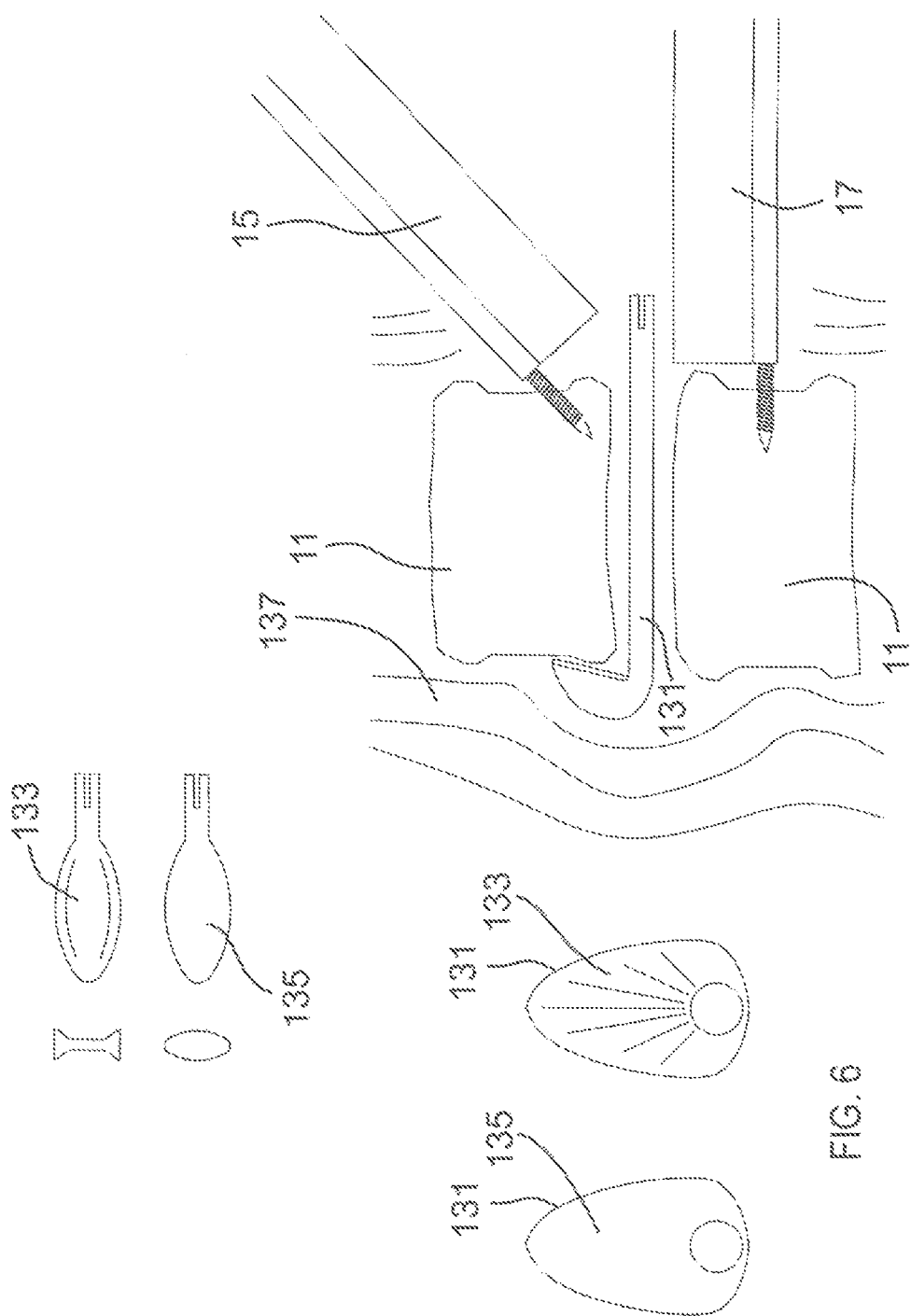

RETRACTOR

CROSS REFERENCE TO RELATED APPLICATIONS

This application claims the benefit of U.S. provisional patent application Ser. No. 61/075,007 filed Jul. 24, 2012.

BACKGROUND OF THE INVENTION

Lateral inter-body fusion has significant advantages over other approaches to the lumbar in that it allows the placement of large inter-body fusion cages that minimize subsidence and allows the correction of scoliosis because contractures of the disc annulus can be released (cut). Currently available retractors for lateral inter-body fusions use two, three or four retractor blades to expose the lateral aspect of the L1-L2, L2-L3, L3-L4 and L4-L5 discs. The L5-S1 disc cannot be currently exposed from a lateral approach. Using the currently available retractor systems, the L1-L2 and L4-L5 discs are often difficult and sometimes impossible to expose for a lateral fusion. The hinged retractor blade and associated equipment are designed to make lateral inter-body cage fusions readily doable at the L1-L2 and L4-L5 levels.

SUMMARY OF THE INVENTION

The proposed retractor blade is designed to function with a number of the currently available retractor systems with only minor modifications to those systems. The retractor blade has a hinge allowing it to flex and thereby allow a lateral approach to the discs at L1-L2 and L4-L5 despite the angle to these discs caused by coming in under the ribs or over the iliac crest.

Other objects and advantages of the present invention will become apparent to those skilled in the art upon a review of the following detailed description of the preferred embodiments and the accompanying drawings.

BRIEF DESCRIPTION OF THE DRAWINGS

FIG. 4 is a side elevational view of a vari angle tool that can be used with the retractor.
FIG. 5 is a side elevational view of a site preparation tool.
FIG. 6 is a front elevational view of the working end of the preparation tool.

DETAILED DESCRIPTION OF THE PREFERRED EMBODIMENT(S)

Figure 1:
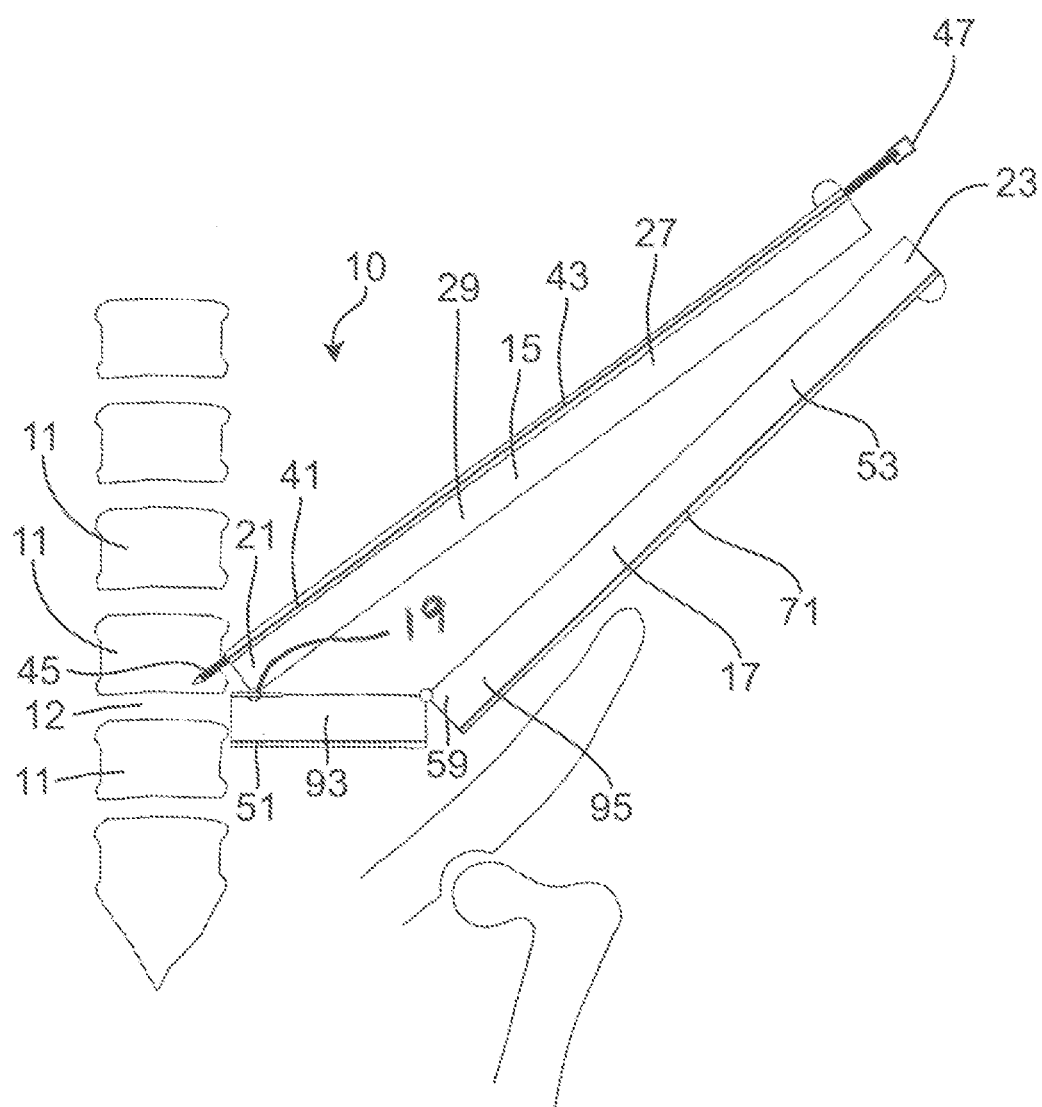
FIG. 1 is a side elevational view of the retractor
Figure 2:
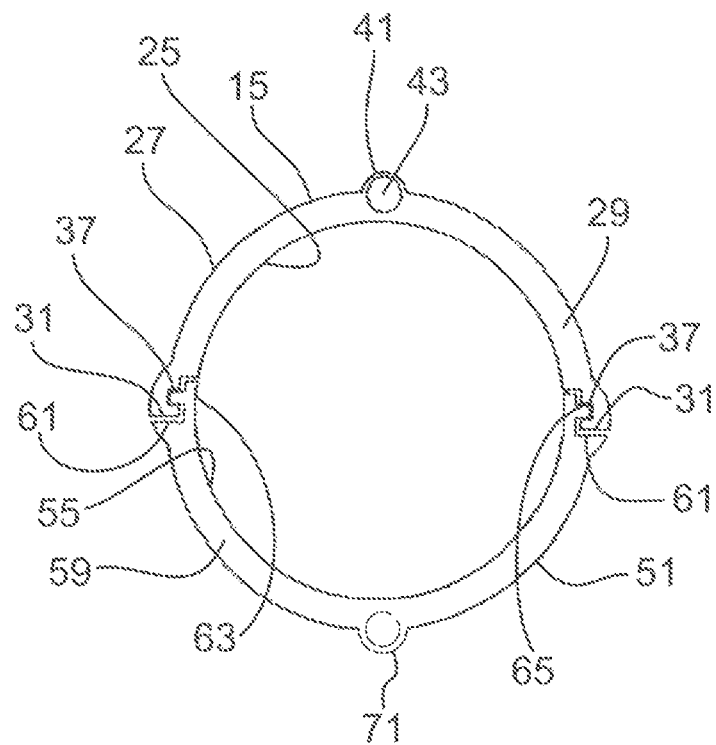
FIG. 2 is a cross sectional view of the invention.

The proposed retractor blade is designed to function with a number of the currently available retractor systems with only minor modifications to those systems. The retractor blade has a hinge allowing it to flex and thereby allow a lateral approach to the discs at L1-L2 and L4-L5 despite the angle to these discs caused by coming in under the ribs or over the iliac crest. The design would incorporate a channel down the back side containing a pin at the bottom to hold the blade against the vertebral body and is attached to a cable and a rod at the top of the channel. The cable retracts into the center of the lower part of the rod. The upper part of the pin prevents the retractor from flexing as it is inserted in a conventional manner with a straight, non-bendable blade and perhaps other blades over a "K" wire and a series of dilating tubes. Once in proper position, as determined with fluoroscopy and electrical stimulation/EMG, and perhaps with the blades of the retractor somewhat opened, the retractor blade, located below the L4-L5 disc or above the L1-L2 disc can be opened. The pin, if desired, can be tapped into the side of the vertebral body by tapping on the rod and pin in the channel in the back of the retractor. The rod can then be lifted past the hinge leaving the cable in the channel. The blade can then be flexed at the hinge and cable by pushing down on the top of the blade, the hinged blade being longer than the others. The blade can then be locked in position to the retractor frame. Side blades can be used to retract soft tissues between the straight and flexed blades if necessary.

The discectomy can be performed, the annulus of the disc opened on each side and the fusion cage inserted with angled instruments. A handle with adjustable locking hinge and interchangeable tool heads such as currets, periosteal elevators and a cage holder are included in the system. It is envisioned that the retractor blades would be radio lucent and disposable.

To remove the retractor, the rod in the channel on the back of the retractor blade is lifted, this in turn pulls on the cable retracting the bone pin and straightening the retractor which can then be withdrawn.

It is thought that this retractor system will expand the utility of the lateral approach to the lumbar spine and its inherent advantages in lumbar fusion.

The retractor 10 of the present invention as shown in FIGS. 1-7 has a first blade 15 and a second blade 17. The first blade has a first end 21 and a second end 23. The first blade 15 has a semi-circular shape and has an interior surface 25 and an exterior surface 27 formed by the sidewall 29 of the first blade 15. The sidewall 29 defines an end region 31 on each side of the first blade 15. A groove 37 is positioned in the interior surface 25 and extends along the entire length of the first blade 15 adjacent the end region 31. A passageway 41 is disposed on the exterior surface 27 of the first blade 15. The passageway 41 extends the length of the first blade 15. It should be appreciated that the groove 37 could be positioned on the exterior and the passageway 41 could be positioned on the interior of the first blade without departing from the scope of the invention. The passageway 41 is usually positioned midway between the two end regions 31 formed by the sidewall 29 of the first blade 15. The passageway 41 extends substantially along the longitudinal axis of the first blade 15. A screw 43 is rotatably mounted in the passageway 41. The screw has an auger portion 45 that extends from the end of the passageway 41 that is adjacent the first end 21 of the first blade 15. The screw 43 has a drive head 47 that is on the end of the screw 43 that is opposite to the auger portion 45. The drive head 47 is adjacent the second end 23 of the first blade 15.

Figure 3:
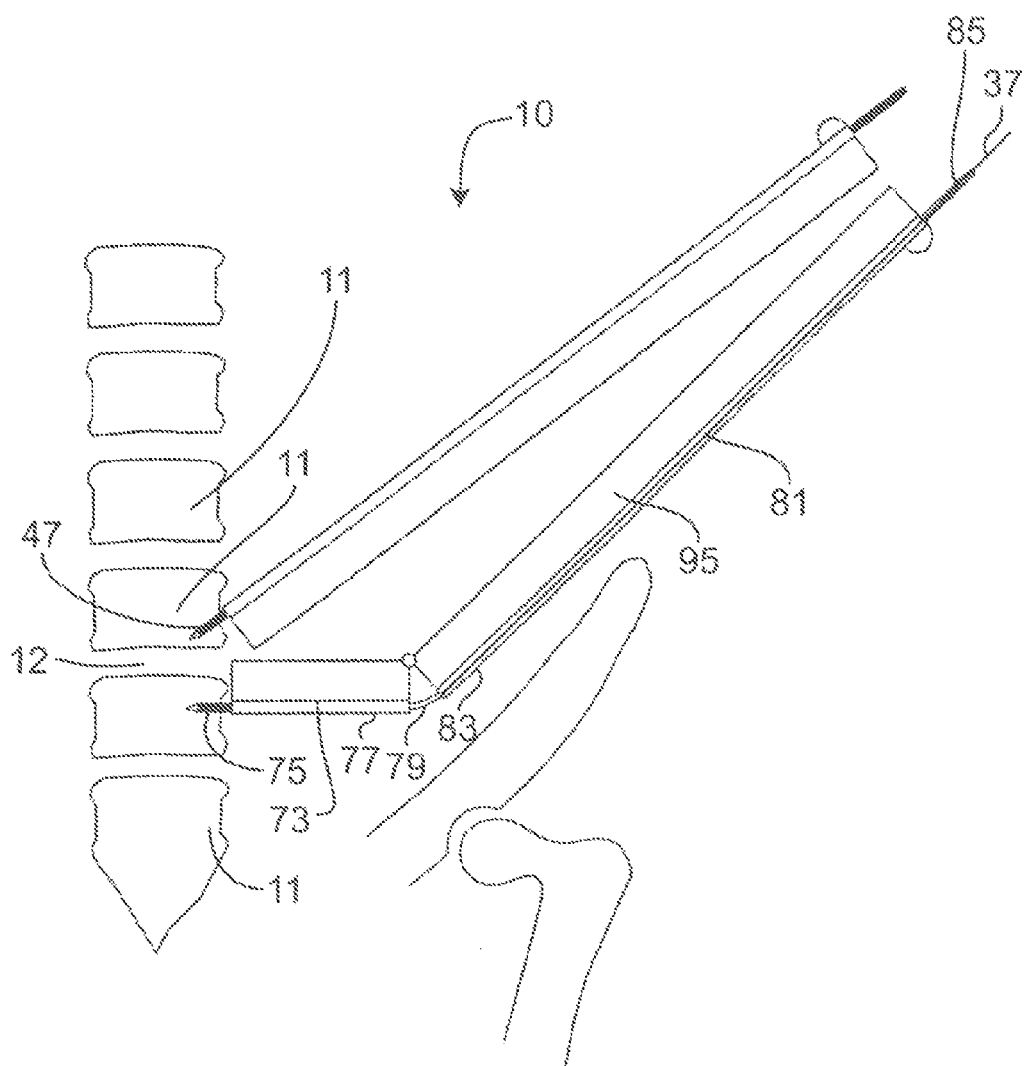
FIG. 3 is a side elevational view of the invention.

The second blade 17 has a semi-circular shape that is substantially the same as the semi-circular shape of the first blade 15. The second blade has a first end 51 and a second end 53. The first end 51 of the second blade can be hinged by secured to the first end 21 of the first blade by a hinge 19. It should be appreciated that the hinge 19 is not required for the proper utilization of the retractor. FIG. 3 shows the retractor 10 without the hinge connection between the first and second blades. As shown in Fig. the first end of the second blade is secured with a pin 73. The second blade defines and interior surface 55 and an exterior surface 57 that are formed by the sidewall 59 of the second blade. The sidewall 59 forms an end region 61 on each side of the second blade 17. A flange 63 extends from each side of the sidewall 59 on the interior surface 55. The flange 63 extends in a direction that is away from the interior surface 55. The flanges 63 are located on the first and second ends of the second blade 17. A pin 65 extends from the flange 63 in a direction that is substantially perpendicular to the flange. The pin 65 located on each side of the second blade 17 are disposed to be in alignment with the groove 37 formed in the first blade 15.

A channel 71 extends along the exterior surfaces 57 of the second blade 17. The channel could also be positioned on the interior of the second blade and not depart from the scope of the invention. The channel is positioned substantially midway between the end regions 61 on the sidewall 59. The channel 71 extends substantially parallel to the longitudinal axis of the second blade 17. A pin 73 is positioned in the channel 71 adjacent to the first end 51 of the second blade 17. The pin 73 has a first end 75 that has a sharp point and is disposed adjacent the first end 51 of the second blade 17. The pin has a second end 77 that is in spaced apart relationship with the first end and extends into the channel 71. A flexible cable 79 is attached to the second end 77 of the pin 73. The flexible cable 79 extends through the channel 71 and extends past the second end 53 of the second blade 17. A hollow lock pin 81 is positioned on the flexible cable 79 and extends into the channel 71. The hollow lock pin has a first end 83 and a second end 85. The first end of the hollow lock pin is positioned in the channel 71 and is constructed so that it can engage the end of the securing pin 73 that is positioned in the channel 71 in spaced apart relationship from the first end 51 of the second blade 17. The second end 85 of the hollow lock pin 81 extends from the end of the channel 71 at the second end 53 of the second blade 17. The first end 83 of the hollow locking pin 81 is designed so that it can engage the securing pin 73 and apply force against the securing pin.

A hinge 91 is positioned on the end region 61 of the second blade 17. The hinge 91 separates the second blade 17 into a first section 93 and second section 95. The hinge 91 allows the first section 93 to pivot with respect to the second section 95.

In operation, the retractor 10 is positioned in the body of a patient to position a fusion cage between the vertebrae 11 and the spine of a patient. The retractor 10 is used with the lateral approach for inserting the fusion cage and it is usually necessary to position the retractor at an angle with respect to the spine of the patient. When the retractor 10 is properly positioned adjacent the space where a disc has been removed from between adjacent vertebrae the auger point 45 on the screw 43 will be adjacent one of the vertebrae 11. The drive head 47 can be engaged to rotate the screw so that the auger head will penetrate the bone of the adjacent vertebrae 11 and secure the first blade 15 with respect to the vertebrae 11. The fusion cage 97 or other spacers can then be positioned in the interior of the retractor 10 between the first blade 15 and the second blade 17. The fusion cage is advanced along the retractor until it is at the first end of the first and second blades. As the retractor 10 is positioned at an angle with respect to the spine the fusion cage will not be in alignment with the space 12 between the adjacent vertebrae 11.

Once the fusion cage is adjacent the first end of the first and second blades the hollow lock pin 81 can be tapped so that the hollow lock pin provides a driving force against the securing pin 73 located in the first section 93 of the second blade 17. The tapping of the hollow lock pin will cause the securing pin 73 to engage the bone of the vertebrae 11 that is adjacent the vertebrae 11 where the auger portion 45 of the screw 43 is secured. The securing pin 73 will secure the first end 51 of the second blade 17 with respect to the vertebrae 11. The hollow lock pin 81 is then advanced in the channel 71 in a direction towards the second end 53 of the second blade 17. When the hollow lock pin 81 has been advanced past the hinge 91 the first section 93 of the second blade 17 can pivot with respect to the second section 95 of the second blade 17. The pivoting action of the first and second sections causes the second blade 17 to move away from the first blade 15. The first section 93 is pivoted until it is substantially in alignment with the space 12 between the adjacent vertebrae 11. With this orientation for the first section 93 the fusion cage will be in alignment with space 12 between the adjacent vertebrae 11. The fusion cage can then be advanced from the first section 93 of the second blade 17 into the space 12. The pivoting motion between the first section 93 and second section 95 of the second blade 17 allows the fusion cage to be properly positioned even though the retractor 10 enters the body of the patient at an angle with respect to the center line of the spine of the patient.

As the first section 93 is pivoted with respect to the second section 95, the first end 53 of the second section will move relative to the second end 23 of the first blade 15. The pins 85 located on the flanges 63 on the second end 53 of the second blade 17 will move along the groove 37 formed in the first blade 15. The relationship between the pins 65 on the second end of the second blade and the groove on the first blade, act to retain the second blade in a desired relationship with the first blade during the pivoting motion of the second blade. This relationship between the first and second blades is maintained even as the second end 53 of the second blade 17 is displaced with respect to the second end 23 of the first blade 15.

When it is time to remove the retractor 10 the flexible cable 79 is pulled tight which will cause the first section 93 come into alignment with the second section 95 of the second blade 17. The hollow lock pin 81 can then be advanced along the channel 71 past the hinge 91 whereby the first section 93 and second section 95 are locked into a position adjacent the first blade 15. The flexible cable then can be pulled to disengage the securing pin 73 from the vertebrae 11 on one side of the space 12. The screw 43 in the passageway 41 on the first blade 15 can then be advanced to disengage the auger portion 45 from the vertebrae 11 on the opposite side of the space 12. Once the auger portion 45 and the securing pin 73 are disengaged from the vertebrae 11 the retractor 10 can be withdrawn from the patient.

A variable angle tool 110 can be used with the retractor of the present invention. The tool 110 has a handle portion 115 and a shaft 117 that extends from the handle. The end 121 of the shaft that is spaced apart from the handle portion 115 has a pivot joint 125. The angle of the pivot can be adjusted by turning a portion of the handle which in turn moves an internal shaft attached to a screw and cog or other mechanism to alter the angle of the pivot. The angle can be locked. A tool end 127 is positioned on the end of the pivot joint that is spaced apart from the handle portion 115. The tool end 127 is designed to accept various tool or components that are used in spinal surgery. A curette head 129 can be positioned on the tool end to clean the space between adjacent vertebrae 11 where a disk has been removed.

Figure 7:
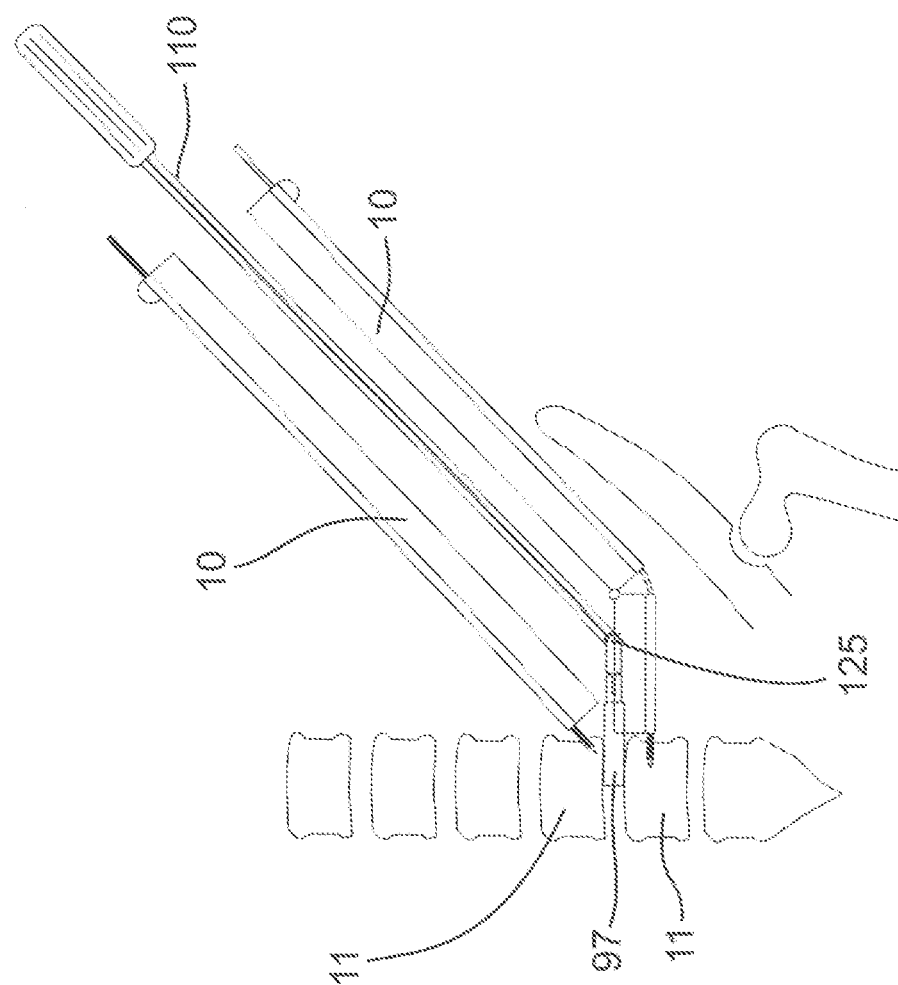
FIG. 7 is a side elevational view of the vari angle tool used to insert a spinal fusion cage.

As shown in FIGS. 5 and 6 a site preparation tool 131 can be attached to the tool end 127. The site preparation tool has a serrated surface 133 that can be used to clean the bone surface and a smooth surface 135 that moves adjacent muscle 137 away from the area that is being cleaned. A disk shaver 133 and a disk distractor 135 can also be attached to the tool end and used as part of the surgical procedure. FIG. 7 shows the use of the variable angle tool 110 to insert a fusion cage 97 into the space between adjacent vertebrae 11 in combination with the retractor 10. Other tools and spacers can also be used with or positioned by the variable angle tool 110. The pivot joint 125 allows the tool to position tools and spacers at an angle with respect to the entry port positioned in a patient and expand the case at which such minimally invasive surgical procedures can be used.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

I claim:

1. A retractor comprising:
    a first blade having a semicircular shape, the first blade having a first end and a second end;
    a second blade having a semicircular shape, the second blade being disposed in opposed aligned relationship with the first blade, the second blade having a first end and a second end, the second blade being disposed relative to the first blade to form a substantially circular passageway;
    a first hinge positioned on the first end of the first and second blades, the hinge pivotally joining the first end of the second blade to the first end of the first blade;
    a second hinge positioned on the second blade, the second hinge being positioned between the first end and the second end of the second blade, the second hinge allowing a portion of the second blade to be disposed at an angle with respect to the first blade, the angle being selected to allow the retractor to position items during surgery.

2. The retractor of claim 1 wherein a second hinge is positioned in spaced apart relationship to the first hinge.

3. The retractor of claim 2 wherein the second hinge is positioned on the portion of the second blade that is from about 10% to about 45% of a length of the second leg from the first hinge.

4. The retractor of claim 1 wherein a screw is rotatably positioned on the first blade, the screw extending from the first end of the first blade, the screw being disposed for engaging a bone in a patient to secure the retractor in position relative to the patient.

5. The retractor of claim 4 wherein the screw is positioned on a side of the first blade that is spaced apart from the second blade.

6. The retractor of claim 5 wherein the screw extends beyond the second end of the first blade, the end of the screw extending beyond the second end having a drive head for rotating the screw.

7. The retractor of claim 1 wherein a locking pin is moveably positioned on the second blade, the locking pin disposed on the portion of the second blade that is spaced apart from the first blade, the locking pin being moveable from a first position that extends beyond the second hinge to a second position that does not extend beyond the second hinge, the locking pin preventing the second hinge from functioning as a hinge when the locking pin is in the first position.

8. The retractor of claim 7 wherein the locking pin extends beyond the second end of the second blade to facilitate movement of the locking pin.

9. The retractor of claim 1 wherein a retaining device is positioned on the second blade to maintain the second blade in the desired hinged position.

10. The retractor of claim 9 wherein the retaining device engages the first blade to secure the second blade in the desired position.

11. The retractor of claim 1 wherein the second blade is moveably attached to the first blade whereby the second end of the second blade is displaced with respect to the second end of the first blade when the second hinge is engaged to allow the portion of the second blade to be disposed at an angle to the first blade.

12. The retractor of claim 8 wherein the locking pin has a tip that extends from the first end of the second blade when the locking pin is in the first position, the tip being disposed to engage a bone on a patient to retain the second blade in a desired positioned.

13. The retractor of claim 12 wherein the tip is retracted into the first end of the second blade when the locking rod is in the second position.

14. The retractor of claim 13 wherein the second blade is in a straight orientation when the locking pin is in the second position, the second position facilitating insertion and removal of the retractor from a patient.

15. The retractor of claim 1 wherein a variable angle tool can be used with the retractor to position tools and replacement parts in a patient.

16. The retractor of claim 15 wherein the variable angle tool has an adjustment mechanism that can adjust the angle of the tool, the adjustment mechanism having a lock to secure the tool in the desired orientation.

17. The retractor of claim 16 wherein the variable angle tool has a tool end that can accommodate various surgical tools.

\* \* \* \* \*